United States Patent [19]
Meierhoefer

[11] 3,989,044
[45] Nov. 2, 1976

[54] SYRINGE

[75] Inventor: Eugene J. Meierhoefer, Hackettstown, N.J.

[73] Assignee: Warner-Lambert Company, Morris Plains, N.J.

[22] Filed: Aug. 11, 1975

[21] Appl. No.: 603,474

[52] U.S. Cl. .............................. 128/218 N; 128/221
[51] Int. Cl.² .......................................... A61M 5/00
[58] Field of Search..... 128/218 R, 218 N, 218 NV, 128/218 D, 218 DA, 220, 221

[56] References Cited
UNITED STATES PATENTS

| 2,828,743 | 4/1958 | Ashkenaz et al. | 128/218 D |
| 3,179,107 | 4/1965 | Clark | 128/221 |
| 3,344,787 | 10/1967 | MacLean | 128/221 |
| 3,825,003 | 7/1974 | Kruck | 128/221 |
| 3,884,229 | 5/1975 | Raines | 128/218 N |

*Primary Examiner*—John D. Yasko
*Attorney, Agent, or Firm*—Albert H. Graddis; Frank S. Chow; George M. Yahwak

[57] ABSTRACT

A prefilled syringe having a barrel to hold a liquid medium is disclosed. The rear end of the barrel is sealed by means of a rubber diaphragm whereas the front end of the syringe is sealed by a stopper and a novel needle hub assembly whereby the integrity of the liquid medium remains static until the assembly is activated and the stopper pierced.

7 Claims, 14 Drawing Figures

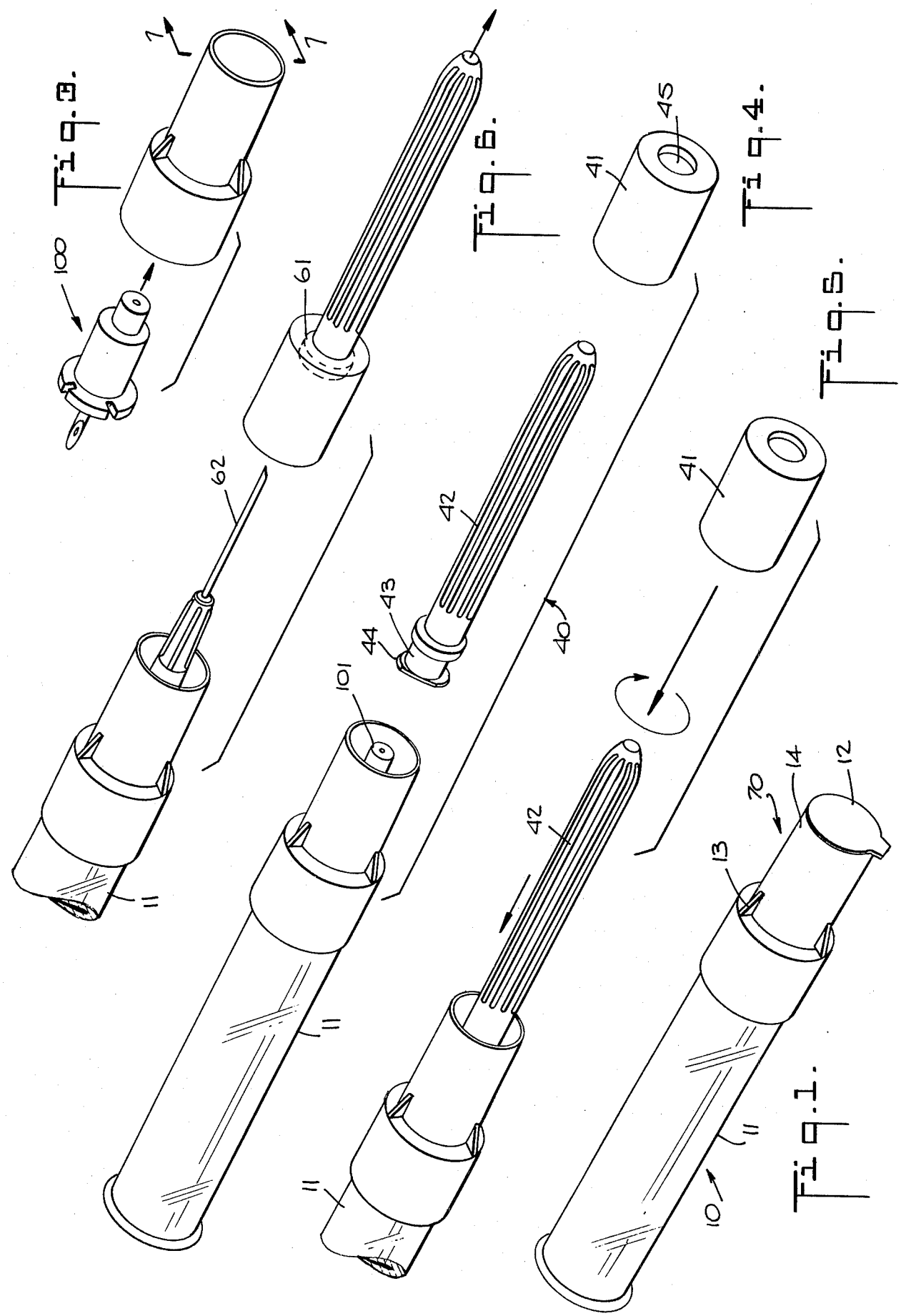

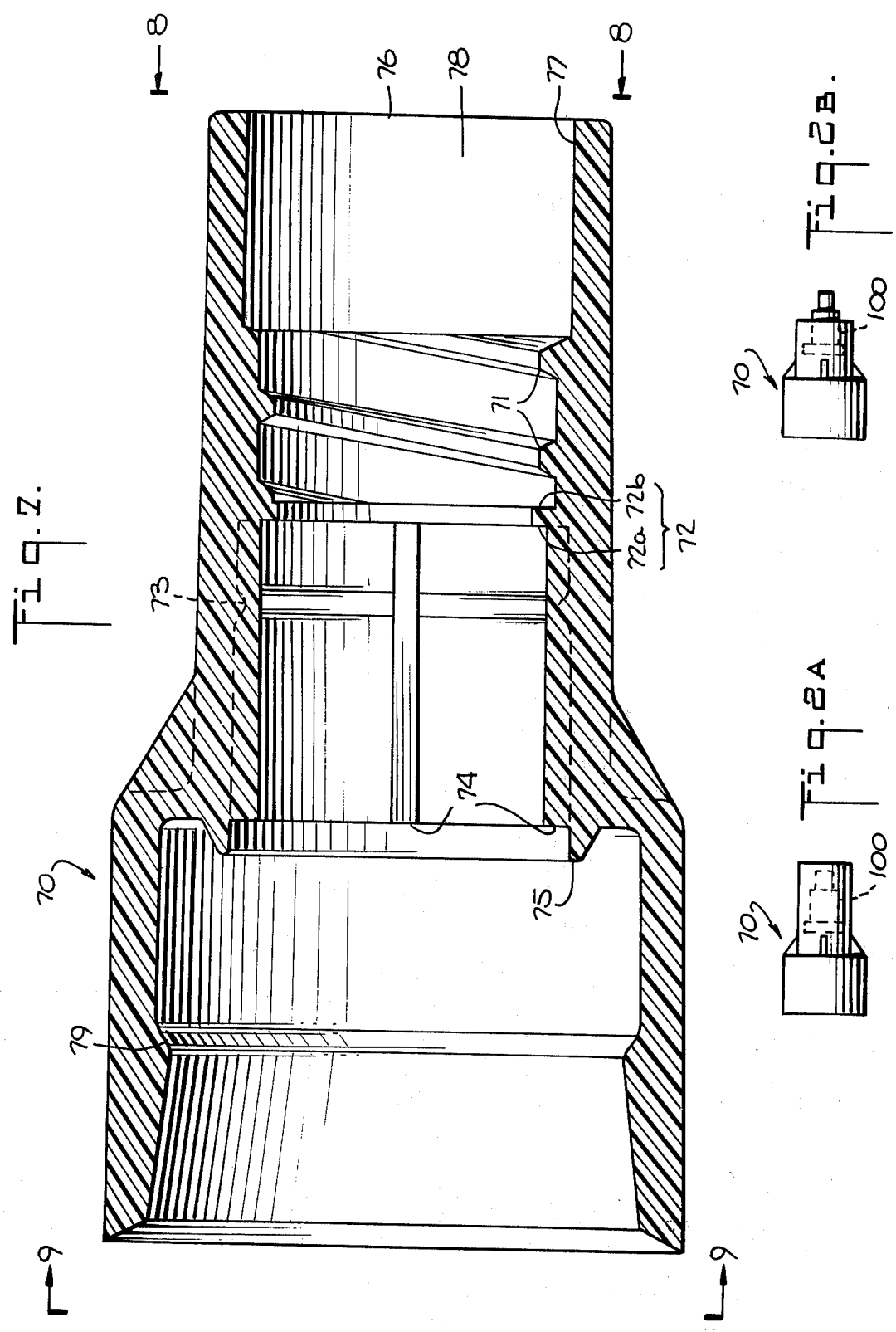

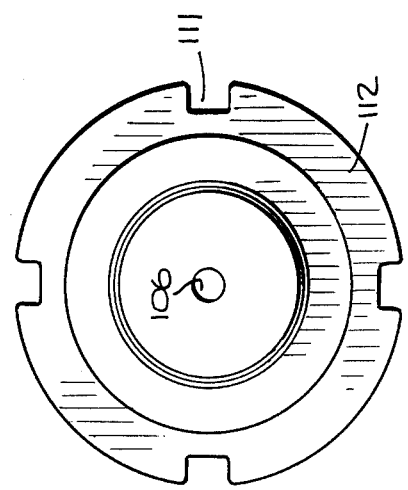
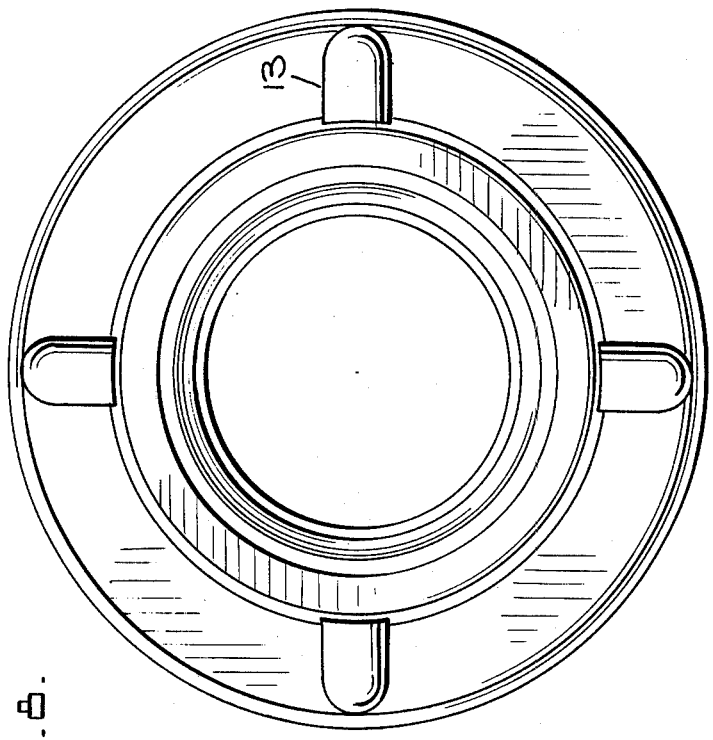
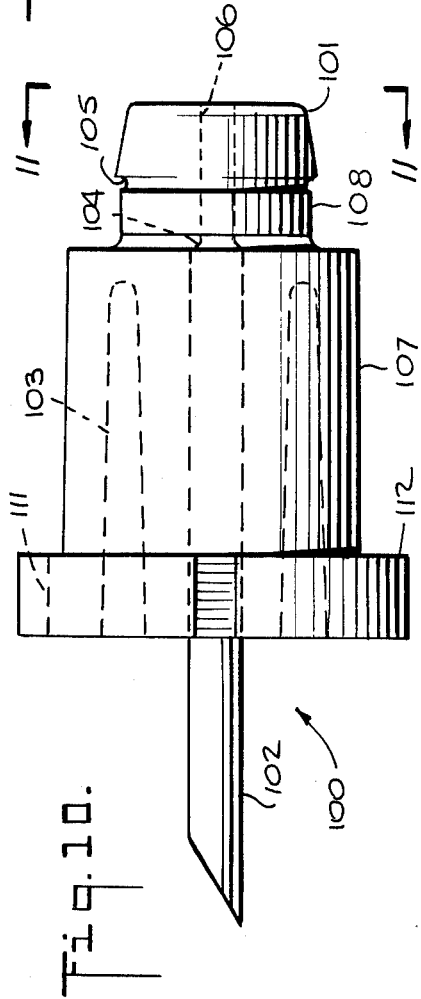
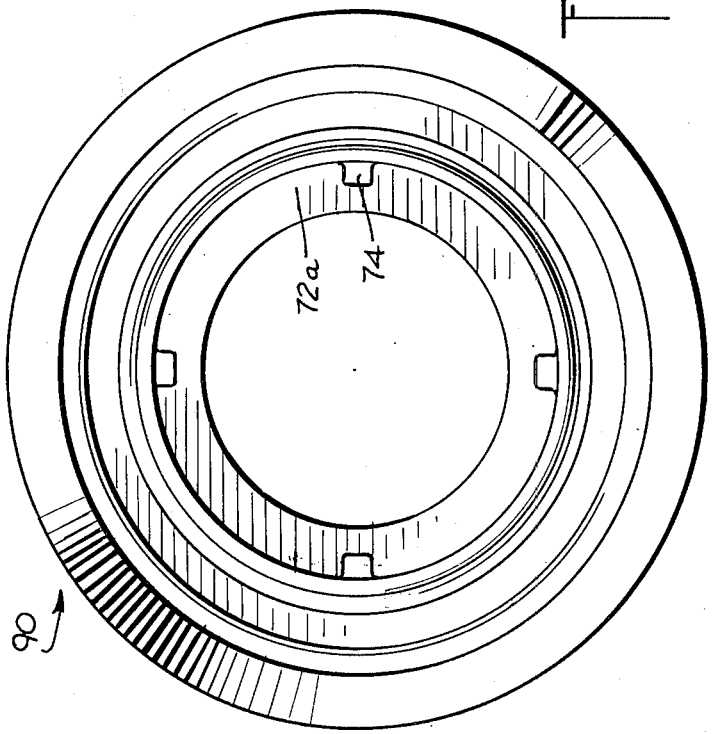

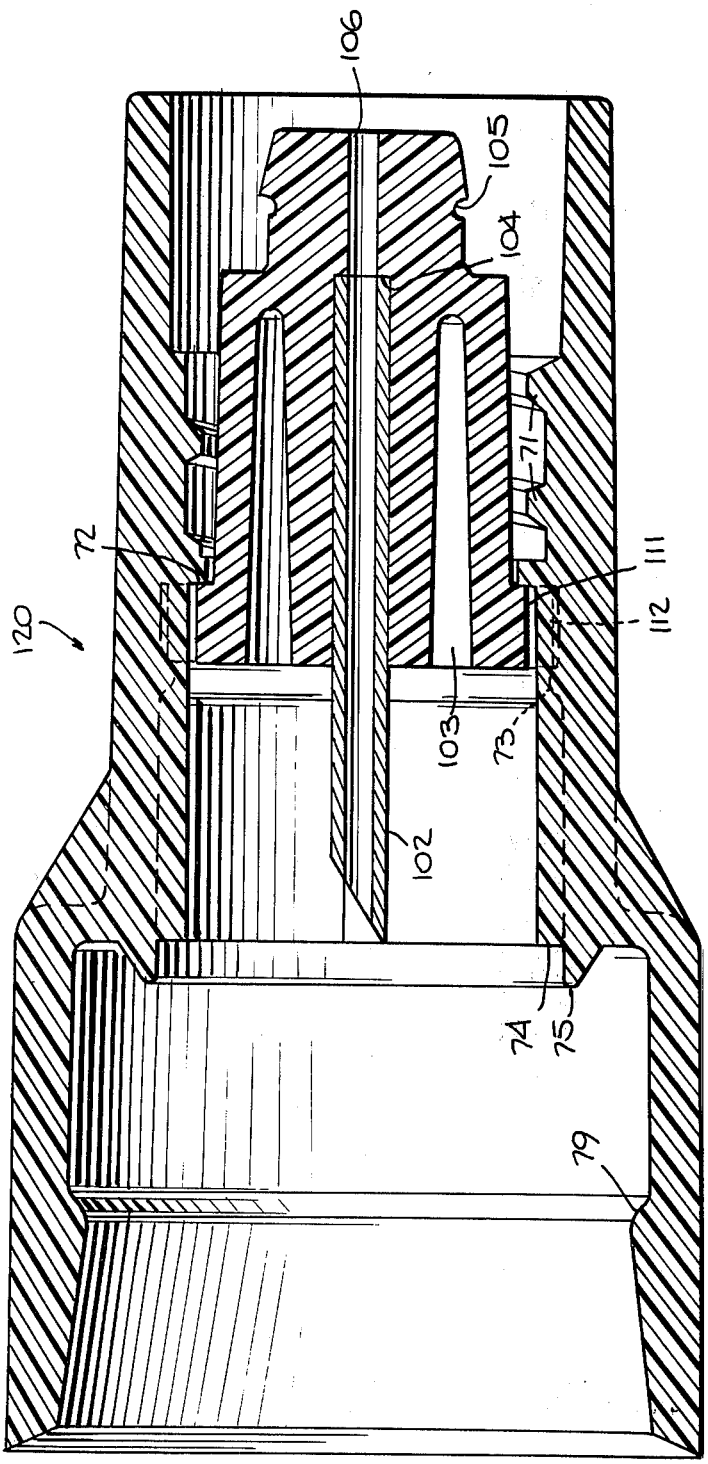

SYRINGE

This invention relates generally to a syringe construction and, more particularly, to a syringe construction providing for a separation of liquid medium or injectable substance and the hypodermic needle to use.

In many instances, it is commercially desirable to pack an injectable substance in a sterile drug delivery system such as a prefilled syringe. Such a syringe, ready for immediate use, has been in great demand and yet attempts to satisfy this demand have not proven satisfactory to meet all of the commercial and safety demands.

It is, therefore, an object of this invention to provide an improved prefilled syringe construction for isolates, the sterile injectable substance, and the hypodermic needle in an improved manner and until an injection is desired.

Another object is to provide an improved needle hub assembly whereby the integrity of the sterile injectable substance contained within a prefilled syringe may be maintained.

Still another object is to provide an improved needle hub assembly which may be attached to a conventional syringe thereby preventing any substance within the syringe from contacting the conventional hypodermic needle until immediately prior to injection.

Still another object is to provide complete versatility of the syringe, i.e., the syringe may be supplied with or without a needle attached to the assembly; the needle size may be changed after activating as, for example, attachment to a device implanted in the patient.

Other objects and advantages will become apparent from the detailed description which is to be taken in conjunction with the accompanying drawings in which:

FIG. 1 is a perspective view of a syringe incorporating the teachings of the present invention;

FIG. 2A is a side elevational view of the needle hub assembly of the present invention;

FIG. 2B is a side elevational view of a modified needle hub assembly of the present invention;

FIG. 3 is an exploded elevational view of the needle hub assembly according to this invention;

FIG. 4 is an exploded perspective view of a prepackaged syringe incorporating the teachings of the present invention;

FIG. 5 is an exploded perspective view of the needle hub assembly of the present invention showing the method of activating the assembly;

FIG. 6 is an exploded perspective view of an activated needle hub assembly according to this invention;

FIG. 7 is a longitudinal cross-sectional view of the needle hub assembly outer piece taken along line 7—7 of FIG. 3;

FIG. 8 is a cross-sectional proximal view of the needle hub assembly outer piece taken along line 8—8 of FIG. 7;

FIG. 9 is view at 9—9 of FIG. 7.

FIG. 10 is a side elevational view of the needle hub assembly inner piece;

FIG. 11 is a cross-sectional proximal view of the needle hub assembly taken along line 11—11 of FIG. 10;

FIG. 12 is a longitudinal cross-sectional view of the needle hub assembly in the non-activated position.

Figure 13:
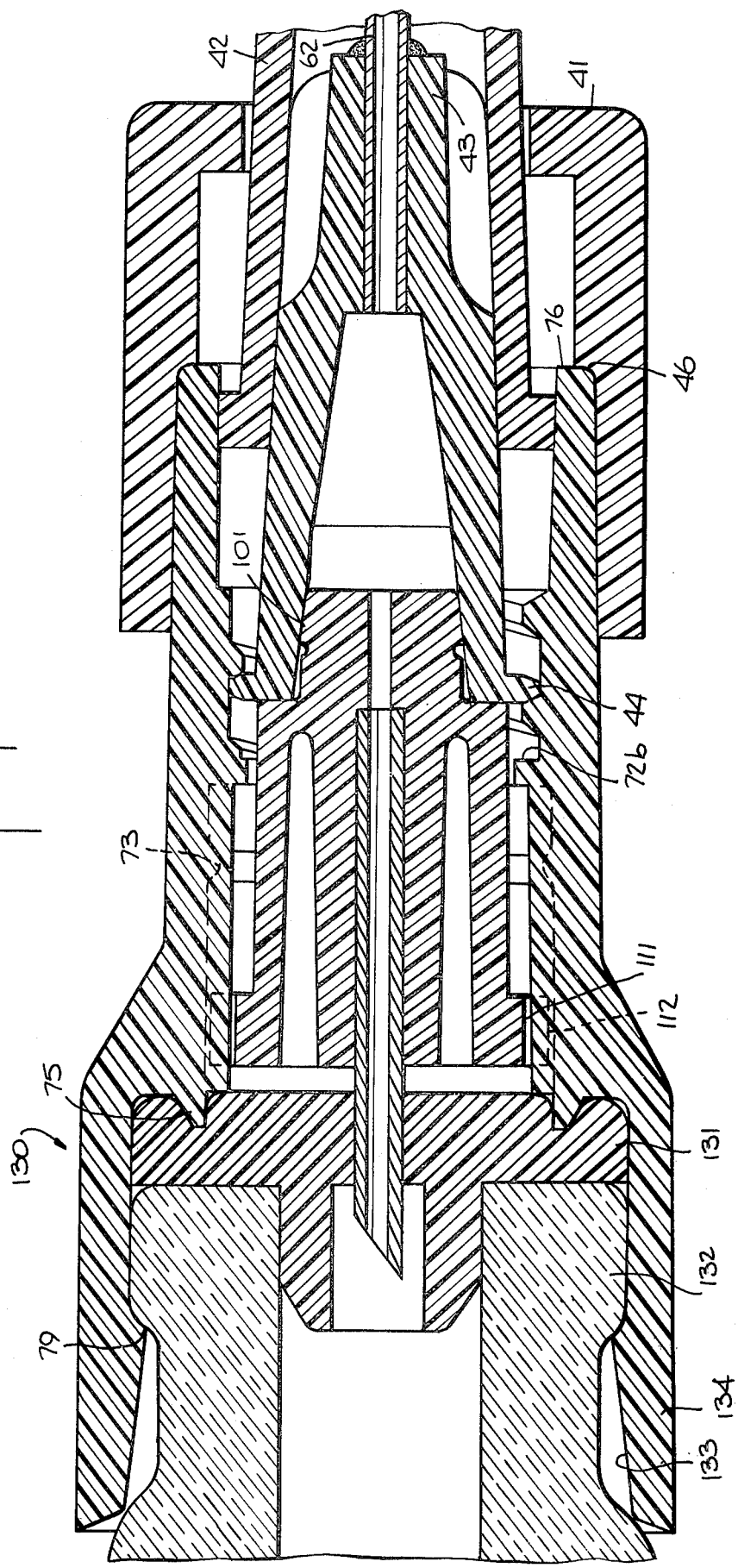
FIG. 13 is a longitudinal cross-sectional view of the needle hub assembly and syringe showing the activated assembly.

In the drawings, the barrel portion 11 of a prefilled syringe 10 is shown in assembled condition with a needle hub assembly 70. As shown in FIG. 1, the assembly is sealed at its proximal end by a tear-cap seal 12 which may be made of any conventionally used sealing material such as paper, foil, or plastic and which is secured by adhesive, heat-sealing, or other means with the understanding that the cap seal effectively allows the sterile inner piece 100 of the assembly to remain sterile until the cap is removed. The outer piece 14 of the needle hub assembly also has a structural strut 13 which is a convenience of manufacture and gives added strength to the unit when the plastic molded unit is ejected from its mold. As will be appreciated, the assembly may of course be made of other materials.

A further method of packing the prefilled syringe is to provide the needle hub assembly with a conventional hypodermic needle and a needle sheath adapter 41. This unit 40 comprises the needle hub assembly, a conventional sterile hypodermic needle encompassed in a needle sheath 42 and being held in place with a needle sheath adapter 41. In this construction, the needle sheath extends through an opening 45 in the needle sheath adapter in such a manner that the flange at the distal end of the needle sheath abuts the inner surface of the needle sheath adapter to form a seal 61 which is capable of maintaining the sterility of the inner piece. The interior shoulder 46 of the adapter fits against the proximal end 76 of the outer piece to further insure a sterile environment for the contents. In this construction, the needle hub 43 rests upon the forward end 101 of the inner piece. This end is a foreshortened luer taper which is tapered to fractionally engage the inner surface of the conventional needle hub. The needle hub flange 44 rides freely within the inner space 78 of the outer piece. In this construction, the syringe is in an inactivated position.

The overall steps in activating the syringe can be seen in FIGS. 4, 5, and 6. The needle sheath is pushed toward the distal end of the adapter and twisted in a clockwise direction. This "screws" the inner piece back against the penetrable diaphragm syringe seal 131 and allows the piercing means 102 of the inner piece to penetrate the diaphram seal. The sheath and the sheath adapter are then discarded as shown in FIG. 6, exposing the cannula 62 of the hypodermic needle.

The inner piece of the assembly as shown in FIG. 10 comprises a distal end which is a locking and stabilizing flange 112 having antirotational grooves 111 therein. The medial portion comprises a cylindrical mass 107 having corings 103 extending from the distal end forwardly. These corings are a convenience of manufacture which although not necessary to the invention have been found to add an outwardly directed spring to the locking and stabilizing flange. The proximal end of the inner piece is comprised of an annular ring portion 108 of reduced diameter and terminating in a friction reducing ring 105 appearing as a groove circumferentially about its distal end. Rearwardly adjacent this groove is a tapered forward end portion 101. Centrally extending through the inner piece is an opening 106, the diameter of which increases to form a seat 104 as the opening enters the cylindrical mass 107 at its junction with the proximal portion. The piercing means of the inner piece is conventionally a cannula having an inner diameter and an outer diameter, the inner diameter of the cannula being equal to the opening through the proximal portion of the inner piece and the outer diameter of the cannula being such that the cannula will tightly engage the inner piece when the cannula abuts the shoulder 104. In this way, the only restriction to the expressability of the liquid within the syringe will be the gauge of the needle used for the injection.

The outer piece of the assembly as shown in FIG. 7 comprises a generally cylindrical body having a proximal end 76 which has an inner space 78 defined by the inner surface 77 of the outer piece and which extends the length of the piece. The inner space immediately adjacent the proximal end is cylindrical in shape and may vary in length as shown in FIGS. 2A and 2B; a different construction of sealing means is obviously required as the length of this area varies.

Immediately distal to this cylindrical shaped area, the inner surface is modified to form a reduced diameter and female threads 71 which extend distally to a stop 72B, the forward face of a circumferentially extending shoulder ring 72. The rear face 72A of the shoulder ring begins a modification of the inner surface to define an inner space equal to the proximal cylindrical shaped area and extending rearwardly a distance equal to the width of the stabilizing flange in the inner piece, limited by the rear face 72A, and a centrally extending retaining ring 73 which forms a shoulder on the inner surface. Extending a distance rearwardly from the rear face of the shoulder ring are four locking and guiding ridges 74 which protrude into the inner space as seen in FIG. 9. Rearwardly of the area defined by these guiding ridges is an internal sealing annular ring 75 extending rearwardly into the cylindrical space adapted to receive the conventional finished needle end 132 of a syringe and the diaphragm syringe seal. Behind this area is a constricted area defining a locking ring 79 for the syringe needle end and an outwardly tapering lead-in area 133 which terminates in an outwardly beveled distal end of the outer piece.

The inner piece fits within the outer piece as a stabilized structure shown in FIG. 12. The retaining flange 112 fits and is locked into the space defined by the shoulder ring 72 and the retaining ring 73. The antirotational grooves fit about the locking and guiding ridges 74.

When assembled, the diaphragm syringe seal 131 will extend about the internal seal ring 75. Thus, the conventional needle end of the syringe and the diaphragm seal will be frictionally locked within the outer piece by the locking ring 79. The stability skirt 134 and the long lead-in area 133 give added stability to the glass and needle tip.

As the needle hub assembly is activated, FIG. 13, the needle sheath 42 is pushed into the assembly 130 thereby breaking the seal 61. This pushing releases the stabilizing flange 112 from the retaining ring 73 and the inner piece is pushed rearwardly with the antirotational grooves riding along the guiding ridges 74. As the needle hub flange 44 engages the female threads 71, it acts as a male thread and allows the operator to screw the inner piece into the outer piece while at the same time correctly fitting the needle hub on the tapered forward end portion 101 of the inner piece. It also allows the piercing means to pierce the diaphragm seal 131. After discarding the needle sheath 42 and the needle sheath adapter 41, the cannula 62 of the needle is exposed and the injectable material within the syringe may be expressed.

I claim:

1. A hypodermic needle, hub and support assembly for attachment to the forward conventional needle flange and extending forward of a transversely extending shoulder of a tubular syringe barrel having a penetrable syringe diaphragm seal, said assembly comprising:

An outer portion having an opening extending throughout its length and having an integral radial annular constructing area defining a locking ring adapted to engage with the rear surface of a conventional forward needle flange, and a stabilizing skirt extending rearwardly from the locking ring to said syringe shoulder and adapted to cooperately relate with the shoulder of the syringe so as to prevent rocking of the assembly with respect to the tubular syringe barrel, and further having a rearwardly extending annular ring forward of said locking ring and adapted to extend into the penetrable syringe diaphragm seal; and an inner portion having a tapered foreshortened front end piece, said taper being such as to cooperate along its length with the interior of a needle hub, a cylindrical midportion and a rear end portion having an outwardly extending flange, and piercing means extending rearwardly from said inner portion and about a central bore extending throughout the length of the inner piece, said bore having the same cross sectional diameter throughout its length.

2. The assembly of claim 1 wherein the inner portion further comprises at least two antirotational grooves extending inwardly from the outer circumferential surface of the flange and wherein the outer portion further comprises at least two longitudinally extending guiding means extending forwardly of the annular seal rings and whereby the cross sectional diameter of the opening and the cross sectional diameter of the rear end portion is such that the inner portion fits within the opening forward of an annular ring by cooperatively engaging the guiding means within the anti-rotational grooves.

3. The assembly of claim 2 wherein the guiding means forward most extension terminates at a stop means and wherein rearwardly of the stop means at a distance substantially equal to the width of the rear end portion flange of the inner portion is located an annular inwardly extending retaining ring adapted to hold the inner portion in the outer portion opening by holding the outer circumferential surface of the inner portion flange in a snap fit cooperation between the stop means and the retaining ring of the outer portion.

4. The assembly of claim 3 which further comprises the outer portion having thread means forward and adjacent to the stop means whereby the distal flange of a hypodermic needle hub may be received and threaded therein.

5. The assembly of claim 3 wherein the outer portion further comprises an integral generally cylindrical opening forward of the stop means and defined by the inner surface of the outer portion whereby the midportion and the tapered front end piece of the inner portion are in the cylindrical opening in a spaced apart relationship from the inner surface of the outer portion when the inner portion is in snap fit cooperation with the outer portion.

6. The assembly of claim 5 which further comprises sealing means at the forward most end of the opening extending through the outer portion, said sealing means being capable of a sterile seal.

7. A prefilled syringe having a needle, hub, and support assembly comprising:

A conventional syringe barrel sealed at both its ends and continuing a sterile injectable substance, the needle end of the syringe barrel having a penetrable diaphragm syringe seal, and A hypodermic needle, hub support assembly attached to the needle flange end of a syringe barrel, said assembly having a radial annular locking ring in intimate engagement with the rear surface of the needle flange end of the syringe barrel and a stabilizing skirt extending rearwardly from said locking ring and in cylindrical relationship about the forward end of the syringe to a point adjacent a transversely extending syringe shoulder and in cooperative relationship with the shoulder of the syringe so as to prevent the rocking of the assembly, and An outer portion having an opening extending throughout its length and having an integral radial annular constricting area defining a locking ring adapted to engage with the rear surface of a conventional forward needle flange and a stabilizing skirt extending rearwardly from the locking ring to said syringe shoulder and adapted to cooperately relate with the shoulder of the syringe so as to prevent rocking of the assembly with respect to the tubular syringe barrel and further having a rearwardly extending annular ring forward of said locking ring and adapted to extend into the penetrable syringe diaphragm seal; and an inner portion having a tapered foreshortened front end piece, said taper being such as to cooperate along its length with the interior of a needle hub, a cylindrical midportion and a rear end portion having an outwardly extending flange, and piercing means extending rearwardly from said inner portion and about a central bore extending throughout the length of the inner piece, said bore having the same cross sectional diameter throughout its length.

* * * * *